(12) United States Patent
Munneke et al.

(10) Patent No.: US 6,434,426 B1
(45) Date of Patent: Aug. 13, 2002

(54) METHOD AND SYSTEM FOR DETERMINING A NOISE FLOOR IN A CARDIAC PACING SYSTEM

(75) Inventors: Jacob Dave Munneke, NR Arnhem (NL); Peter W. Wohlgemuth, Neukirchen (DE); Harry W. M. De Bruyn, BN Arnhem; Anton L. Huijnen, BS Velp, both of (NL)

(73) Assignee: Medtronic Inc., Minneapolis, MN (US)

( * ) Notice: Subject to any disclaimer, the term of this patent is extended or adjusted under 35 U.S.C. 154(b) by 0 days.

(21) Appl. No.: 09/559,052

(22) Filed: Apr. 27, 2000

(51) Int. Cl.[7] .................................. A61N 1/37
(52) U.S. Cl. ................ 607/27; 607/9; 128/901
(58) Field of Search ................ 607/4, 9, 27, 28; 600/509, 510, 521; 128/901

(56) References Cited

U.S. PATENT DOCUMENTS

| | | |
|---|---|---|
| 4,880,004 A | 11/1989 | Baker et al. |
| 5,103,819 A | 4/1992 | Baker et al. |
| 5,564,430 A | 10/1996 | Jacobson et al. |
| 5,755,738 A | 5/1998 | Kim et al. |
| 6,029,086 A * | 2/2000 | Kim et al. ............... 607/9 |
| 6,029,087 A | 2/2000 | Wohlgemuth |

\* cited by examiner

*Primary Examiner*—George R. Evanisko
(74) *Attorney, Agent, or Firm*—Thomas F. Woods; Thomas G. Berry (57) ABSTRACT

A method for determining a representative noise floor in a cardiac pacing system from which future events are measured is provided. An event amplitude is determined. Pluralities of noise levels are recorded, when each of the plurality of noise levels is less than a predetermined percentage of the event amplitude. The noise floor is determined as an absolute maximum value of the plurality of recorded noise levels.

24 Claims, 7 Drawing Sheets

METHOD AND SYSTEM FOR DETERMINING A NOISE FLOOR IN A CARDIAC PACING SYSTEM

FIELD OF THE INVENTION

The present invention relates to cardial pacing systems, and, in particular, to cardial pacing systems for detecting low amplitude noise and determining a representative noise floor in a cardiac pacing system.

BACKGROUND OF THE INVENTION

Implantable cardiac pacemakers must accurately process sensed signal information so as to determine when a genuine cardiac signal has, in fact, been sensed. Furthermore, implantable cardiac pacemakers must also accurately identify or classify the signal. Separating cardiac signals from polarization effects and other noise artifacts has always been a substantial problem, and a great deal of effort has been placed on improving input circuits for this purpose. Additionally, it is recognized that it is important to be able to classify a sensed signal, e.g., determine whether it is a QRS, P-wave, far field R-wave (FFRW), etc. Many prior art techniques have been developed for signal classification, but improvement is still needed. For example, one prior art technique establishes a variable timing window, and classifies the event in terms of the timing of the signal received during window. However, early beats; ectopic signals, etc. can fool such a technique, and noise can still mask the signal which is sensed within the window. Other known techniques include morphology analysis, comparisons in the time and frequency domain, etc. While many of these techniques provide reasonably good results, they can involve considerable circuit complexity and frequently do not eliminate the probability of error due to the detection of noise or other artifacts.

The advent of digital signal processing (DSP) has provided a tool which can be very useful in the environment of an implanted medical device, e.g., an implanted pacemaker. In DSP technology, the incoming sense signal is converted to a digital signal, e.g., an 8 bit signal at a predetermined sample rate. Successive digital signals can be processed with high reliability and in a manner which is essentially hardware-controlled by the DSP circuitry. More recently, DSP technology has advanced so as to provide the possibility of a low current chip which may be used in an implantable pacemaker to provide significant sensed signal processing capability.

The utilization of a DSP chip for an implantable pacemaker makes available an enhanced capability of processing sensed signals, so as to enable a more accurate classification of a sensed signal. Such DSP processing, together with a processor and an appropriate signal classification algorithm, can provide a powerful tool for accurately sensing and classifying intracardiac signals. In addition to this combined hardware and software capability, there is a need to provide an optimum decision algorithm for using the DSP-generated signal parameters so as to accurately and reliably classify sensed intracardiac signals.

The invention disclosed in U.S. Pat. No. 6,029,087, issued to Wohlgemuth, discloses a DSP solution for sensing a sensed event classification. Wohlgemuth presents a method which includes steps for digitizing a cardiac signal using low power ADC; digitally filtering and calculating a slope; determining a sense when both the filtered signal and the slope are above a predetermined threshold; finding local minimum and maximum points on both the filtered signal and the slope signal during a window period which follows the sense period; and classifying an event by timing the minimum and maximum points during that window.

The invention disclosed in U.S. Pat. No. 5,755,738, issued to Kim et al, discloses an automatic sensing level adjustment means for implantable cardiac rhythm management. In Kim, a sense threshold is set at a fraction of an average peak amplitude of two preceding events. An event threshold is then set at a smaller fraction of the sense threshold. If an additional event exceeds both thresholds, a cardiac event is then differentiated from the noise.

In U.S. Pat. No. 5,564,430, issued to Jacobson et al, a sensing threshold is set at a predetermined fraction of a measured sensed signal. If a further signal is sensed during a "noise refractory interval," the refractory interval is restarted and the sense threshold is incremented.

Finally, in U.S. Pat. Nos. 5,103,819 and 4,880,004, both issued to Baker et al, an invention is disclosed which describes a marathon auto sensing automatic sensitivity adjustment. This sensitivity adjustment utilizes an automated gain control device to control the signal amplitude between a minimum and maximum threshold.

As discussed above, the most pertinent prior art patents are:

TABLE 1

| Prior Art Patents. | | |
|---|---|---|
| U.S. Pat. No. | Date | Inventor(s) |
| 6,029,087 | 02-22-00 | Wohlgemuth |
| 5,755,738 | 05-26-98 | Kim et al. |
| 5,564,430 | 10-15-96 | Jacobson et al. |
| 5,103,819 | 04-14-92 | Baker et al. |
| 4,880,004 | 11-14-89 | Baker et al. |

All patents listed in Table 1 are hereby incorporated by reference herein in their respective entireties. As those of ordinary skill in the art will appreciate readily upon reading the Summary of the Invention, the Detailed Description of the Preferred Embodiments and the Claims set forth below, many of the devices and methods disclosed in the patents of Table 1 may be modified advantageously by using the teachings of the present invention.

SUMMARY OF THE INVENTION

The present invention is therefore directed to providing a method for determining a noise floor in a cardiac pacing system. Such a system of the present invention overcomes the problems, disadvantages and limitations of the prior art described above, and provides a more efficient and accurate means of both detecting and determining a noise floor.

The present invention has certain objects. That is, various embodiments of the present invention provide solutions to one or more problems existing in the prior art respecting the determination of a noise floor. Those problems include, without limitation: receiving a signal corresponding to a level of background noise, determining whether the absolute value of the received level of background noise is greater than a previously recorded version of background noise, and setting a noise floor when an appropriate number of satisfactory measurements have been taken.

In comparison to known techniques for stimulating the contraction of an atrium and/or ventricle of a mammalian heart, various embodiments of the present invention may provide one or more of the following advantages: receiving a signal corresponding to a level of background noise, determining whether the absolute value of the received level of background noise is greater than a previously recorded version of background noise, and setting a noise floor when an appropriate number of satisfactory measurements have been taken.

Some of the embodiments of the present invention include one or more of the following features: an implantable medical device including a processor, a controller operably connected to the processor and at least one sensing lead operably connected to the controller, wherein a noise floor is determined by the processor as an absolute maximum value of a plurality of recorded noise levels received by the processor from the at least one sensing lead, each of the plurality of recorded noise levels being below a percentage.

Furthermore, in accordance with the present invention a method for determining a representative noise floor in a cardiac pacing system from which future events are measured is provided. An event amplitude is determined. Pluralities of noise levels are recorded, when each of the plurality of noise levels is less than a predetermined percentage of the event amplitude. The noise floor is determined as an absolute maximum value of the plurality of recorded noise levels.

Therefore, the algorithm of the present invention enables the implantable medical device to detect and determine a noise floor by measuring the background noise of a mammalian heart and setting the absolute value of that background noise to be a representative noise floor. In this way it is possible to more accurately detect sensed events within the mammalian heart while not being distracted from mirror background noise.

BRIEF DESCRIPTION OF THE DRAWINGS

The above, and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PRESENTLY PREFERRED EMBODIMENTS

Figure 1:
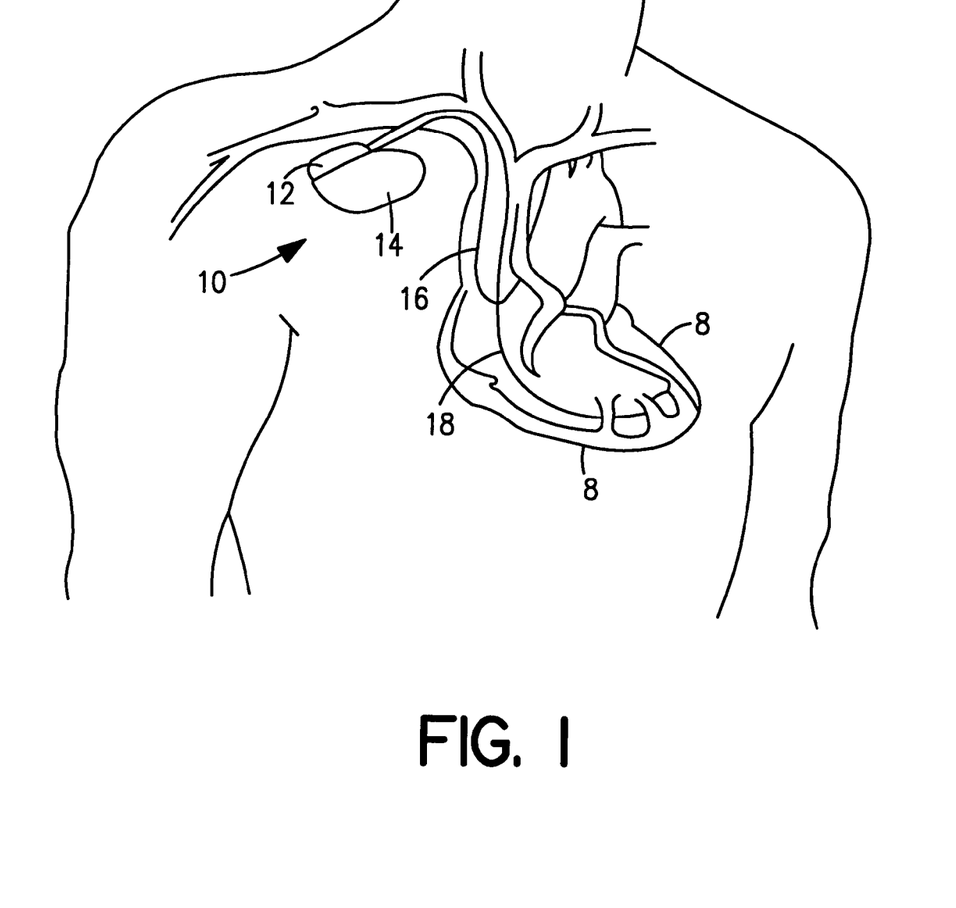
FIG. 1 is a schematic view of an implantable medical device, made in accordance with the present invention.

FIG. 1 is a simplified schematic view of one embodiment of implantable medical device ("IMD") 10 of the present invention. The IMD 10 shown in FIG. 1 is a pacemaker comprising at least one of pacing and sensing leads 16 and 18 attached to hermetically sealed enclosure 14 and implanted near human or mammalian heart 8. Pacing and sensing leads 16 and 18 sense electrical signals attendant to the depolarization and re-polarization of the heart 8, and further provide pacing pulses for causing depolarization of cardiac tissue in the vicinity of the distal ends thereof. Leads 16 and 18 may have unipolar or bipolar electrodes disposed thereon, as is well known in the art. Examples of IMD 10 include implantable cardiac pacemakers disclosed in U.S. Pat. No. 5,158,078 to Bennett et al., U.S. Pat. No. 5,312,453 to Shelton et al. or U.S. Pat. No. 5,144,949 to Olson, all hereby incorporated by reference herein, each in its respective entirety.

Figure 2:
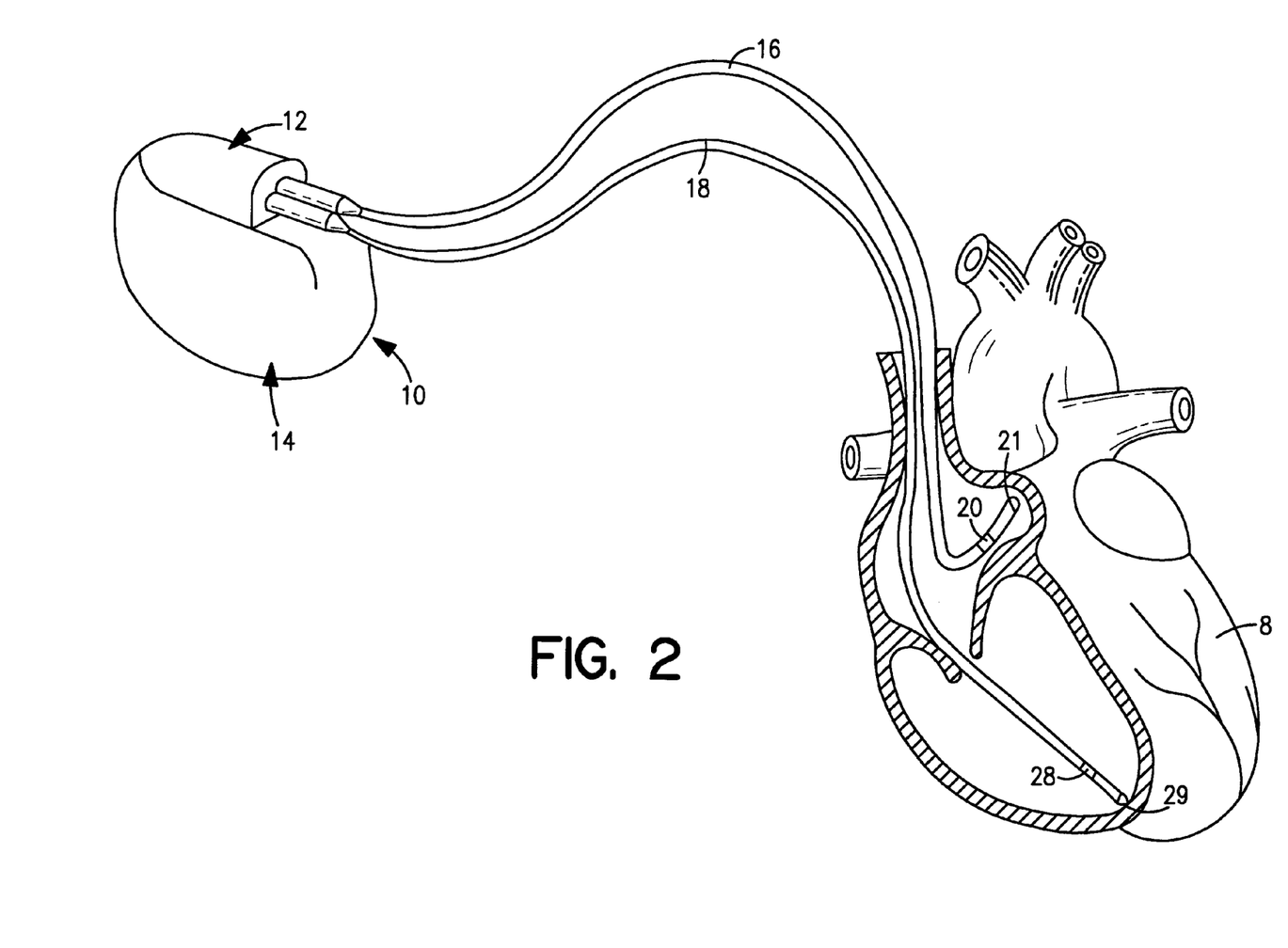
FIG. 2 is another view of the implantable medical device of FIG. 1, made in accordance with the present invention.

FIG. 2 shows connector module 12 and hermetically sealed enclosure 14 of IMD 10 located in and near human or mammalian heart 8. Atrial and ventricular pacing leads 16 and 18 extend from connector header module 12 to the right atrium and ventricle, respectively, of heart 8. Atrial electrodes 20 and 21 disposed at the distal end of atrial pacing lead 16 are located in the right atrium. Ventricular electrodes 28 and 29 at the distal end of ventricular pacing lead 18 are located in the right ventricle.

Figure 3:
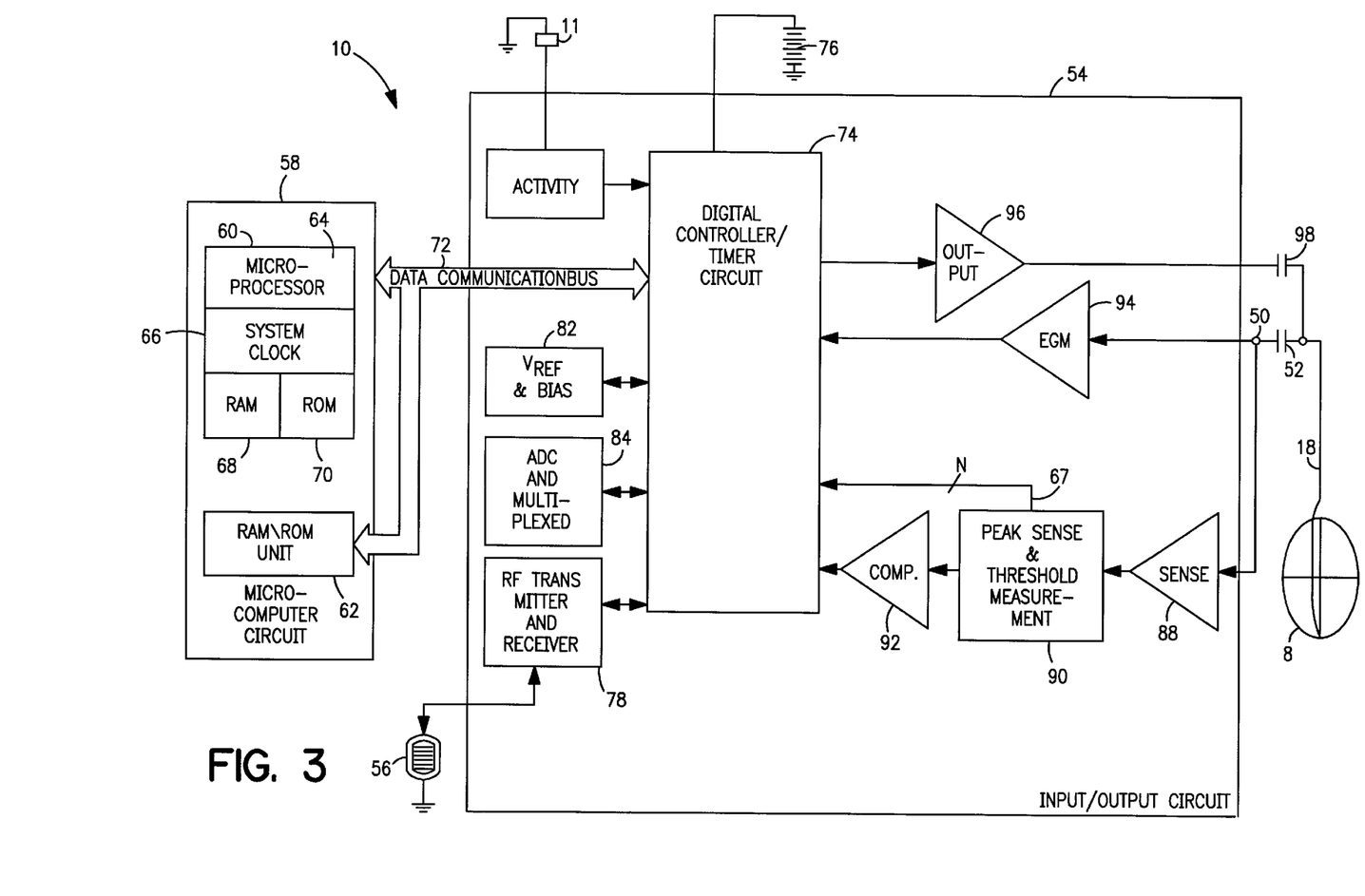
FIG. 3 shows a block diagram illustrating the components of the implantable medical device of FIG. 1, made in accordance with the present invention.

FIG. 3 shows a block diagram illustrating the constituent components of IMD 10 in accordance with one embodiment of the present invention, where IMD 10 is a pacemaker having a processor-based architecture. IMD 10 is shown as including activity sensor or accelerometer 11, which is preferably a piezoceramic accelerometer bonded to a hybrid circuit located inside enclosure 14. Activity sensor 11 typically (although not necessarily) provides a sensor output that varies as a function of a measured parameter relating to a patient's metabolic requirements. For the sake of convenience, IMD 10 in FIG. 3 is shown with lead 18 only connected thereto; similar circuitry and connections not explicitly shown in FIG. 3 apply to lead 16.

IMD 10 in FIG. 3 is most preferably programmable by means of an external programming unit (not shown in the Figures). One such programmer is the commercially available Medtronic/Vitatron Model 9790 programmer, which is processor-based and provides a series of encoded signals to IMD 10, typically through a programming head which transmits or telemeters radio-frequency (RF) encoded signals to IMD 10. Such a telemetry system is described in U.S. Pat. No. 5,312,453 to Wyborny et al., hereby incorporated by reference in its entirety. The programming methodology disclosed in Wyborny et al.'s '453 patent is identified herein for illustrative purposes only. Any of a number of suitable programming and telemetry methodologies known in the art may be employed so long as the desired information is transmitted to and from the pacemaker.

As shown in FIG. 3, lead 18 is coupled to node 50 in IMD 10 through input capacitor 52. Activity sensor or accelerometer 11 is most preferably attached to a hybrid circuit located inside hermetically sealed enclosure 14 of IMD 10. The output signal provided by activity sensor 11 is coupled to input/output circuit 54. Input/output circuit 54 contains analog circuits for interfacing to heart 8, activity sensor 11, antenna 56 and circuits for the application of stimulating pulses to heart 8. The rate of heart 8 is controlled by software-implemented algorithms stored microcomputer circuit 58.

Microcomputer circuit 58 preferably comprises on-board circuit 60 and off-board circuit 62. Circuit 58 may correspond to a microcomputer circuit disclosed in U.S. Pat. No. 5,312,453 to Shelton et al., hereby incorporated by reference in its entirety. On-board circuit 60 preferably includes processor 64, system clock circuit 66 and on-board RAM 68, and ROM 70. Off-board circuit 62 preferably comprises a RAM/ROM unit. On-board circuit 60 and off-board circuit 62 are each coupled by data communication bus 72 to digital controller/timer circuit 74. Microcomputer circuit 58 may comprise a custom integrated circuit device augmented by standard RAM/ROM components.

Electrical components shown in FIG. 3 are powered by an appropriate implantable battery power source 76 in accordance with common practice in the art. For the sake of clarity, the coupling of battery power to the various components of IMD 10 is not shown in the Figures. Antenna 56 is connected to input/output circuit 54 to permit uplink/downlink telemetry through RF transmitter and receiver telemetry unit 78. By way of example, telemetry unit 78 may correspond to that disclosed in U.S. Pat. No. 4,566,063, issued to Thompson et al. and hereby incorporated by reference in its entirety, or to that disclosed in the above-referenced '453 patent. It is generally preferred that the particular programming and telemetry scheme selected permit the entry and storage of cardiac rate-response parameters. The specific embodiments of antenna 56, input/output circuit 54 and telemetry unit 78 presented herein are shown for illustrative purposes only, and are not intended to limit the scope of the present invention.

Continuing to refer to FIG. 3, $V_{REF}$ and Bias circuit 82 most preferably generates stable voltage reference and bias currents for analog circuits included in input/output circuit 54. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled by data communication bus 72 to digital controller/timer circuit 74, where digital timers and counters establish the overall escape interval of the IMD 10 as well as various refractory, blanking and other timing windows for controlling the operation of peripheral components disposed within input/output circuit 54.

Digital controller/timer circuit 74 is preferably coupled to sensing circuitry, including sense amplifier 88, peak sense and threshold measurement unit 90 and comparator/threshold detector 92. Circuit 74 is further preferably coupled to electrogram (EGM) amplifier 94 for receiving amplified and processed signals sensed by lead 18. Sense amplifier 88 amplifies sensed electrical cardiac signals and provides an amplified signal to peak sense and threshold measurement circuitry 90, which in turn provides an indication of peak sensed voltages and measured sense amplifier threshold voltages on multiple conductor signal path 67 to digital controller/timer circuit 74. An amplified sense amplifier signal is then provided to comparator/threshold detector 92. By way of example, sense amplifier 88 may correspond to that disclosed in U.S. Pat. No. 4,379,459 to Stein, hereby incorporated by reference in its entirety.

The electrogram signal provided by EGM amplifier 94 is employed when IMD 10 is being interrogated by an external programmer to transmit a representation of a cardiac analog electrogram. See, for example, U.S. Pat. No. 4,556,063 to Thompson et al., hereby incorporated by reference herein in its entirety. Output pulse generator 96 provides pacing stimuli to patient's heart 8 through coupling capacitor 98 in response to a pacing trigger signal provided by digital controller/timer circuit 74 each time the escape interval times out, an externally transmitted pacing command is received or in response to other stored commands as is well known in the pacing art. By way of example, output ampli-fier 96 may correspond generally to an output amplifier disclosed in U.S. Pat. No. 4,476,868 to Thompson, hereby incorporated by reference in its entirety.

The specific embodiments of input amplifier 88, output amplifier 96 and EGM amplifier 94 identified herein are presented for illustrative purposes only, and are not intended to be limiting in respect of the scope of the present invention. The specific embodiments of such circuits may not be critical to practicing some embodiments of the present invention so long as they provide means for generating a stimulating pulse and are capable of providing signals indicative of natural or stimulated contractions of heart 8.

In some preferred embodiments of the present invention, IMD 10 may operate in various non-rate-responsive modes, including, but not limited to, DDD, DDI, VVI, VOO and VVT modes. In other preferred embodiments of the present invention, IMD 10 may operate in various rate-responsive, including, but not limited to, DDDR, DDIR, VVIR, VOOR and VVTR modes. Some embodiments of the present invention are capable of operating in both non-rate-responsive and rate responsive modes. Moreover, in various embodiments of the present invention IMD 10 may be programmably configured to operate so that it varies the rate at which it delivers stimulating pulses to heart 8 only in response to one or more selected sensor outputs being generated. Numerous pacemaker features and functions not explicitly mentioned herein may be incorporated into IMD 10 while remaining within the scope of the present invention.

The present invention is not limited in scope to single-sensor or dual-sensor pacemakers, and is further not limited to IMD's comprising activity or pressure sensors only. Nor is the present invention limited in scope to single-chamber pacemakers, single-chamber leads for pacemakers or single-sensor or dual-sensor leads for pacemakers. Thus, various embodiments of the present invention may be practiced in conjunction with more than two leads or with multiple-chamber pacemakers, for example. At least some embodiments of the present invention may be applied equally well in the contexts of single-, dual-, triple- or quadruple-chamber pacemakers or other types of IMD's. See, for example, U.S. Pat. No. 5,800,465 to Thompson et al., hereby incorporated by reference herein in its entirety, as are all U.S. Patents referenced therein.

IMD 10 may also be a pacemaker-cardioverter-defibrillator ("PCD") corresponding to any of numerous commercially available implantable PCD's. Various embodiments of the present invention may be practiced in conjunction with PCD's such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless and U.S. Pat. No. 4,821,723 to Baker et al., all of which are hereby incorporated by reference, each in their respective entireties.

Figure 4:
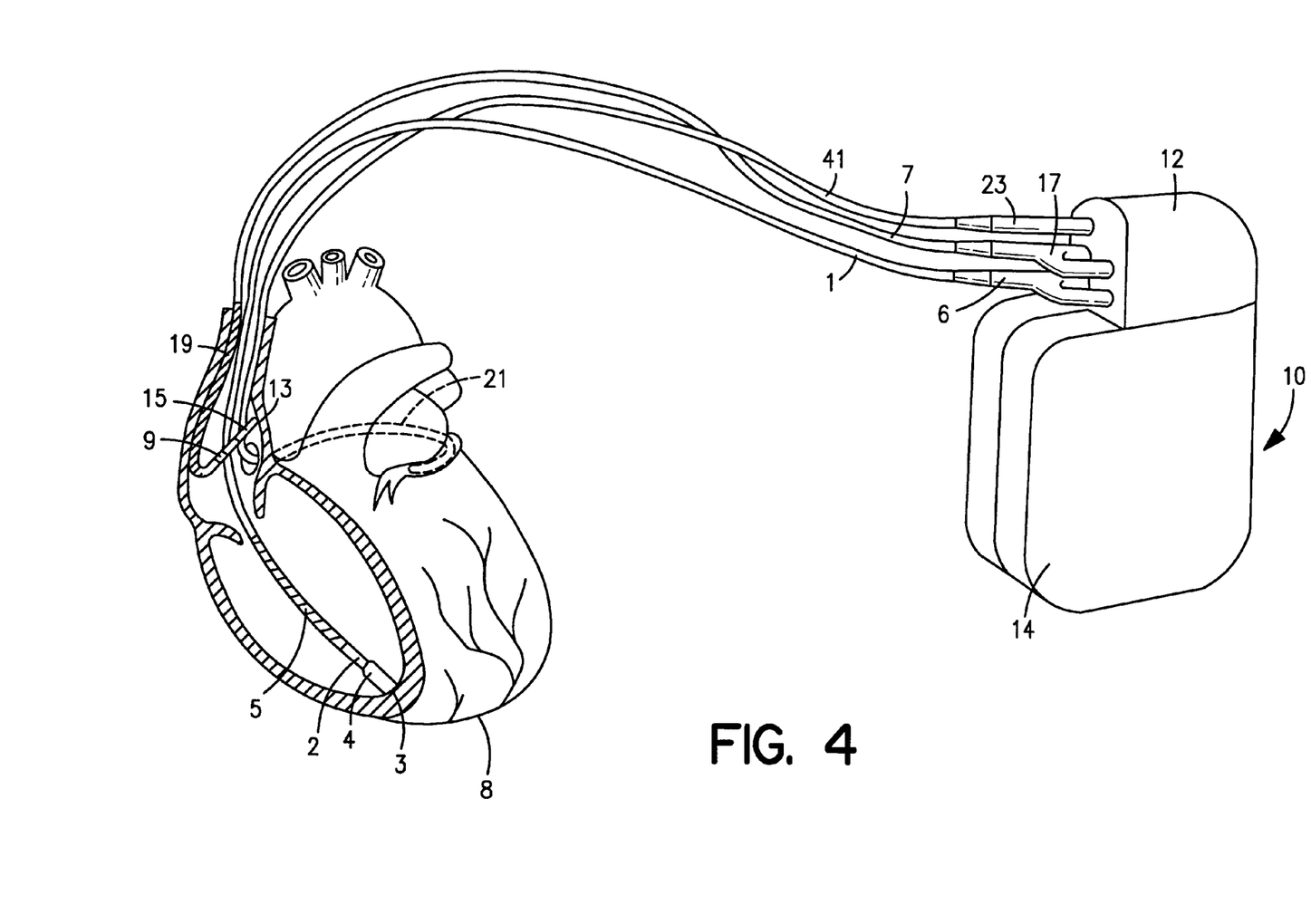
FIG. 4 illustrates another embodiment of the implantable medical device of FIG. 1, made in accordance with the present invention.
Figure 5:
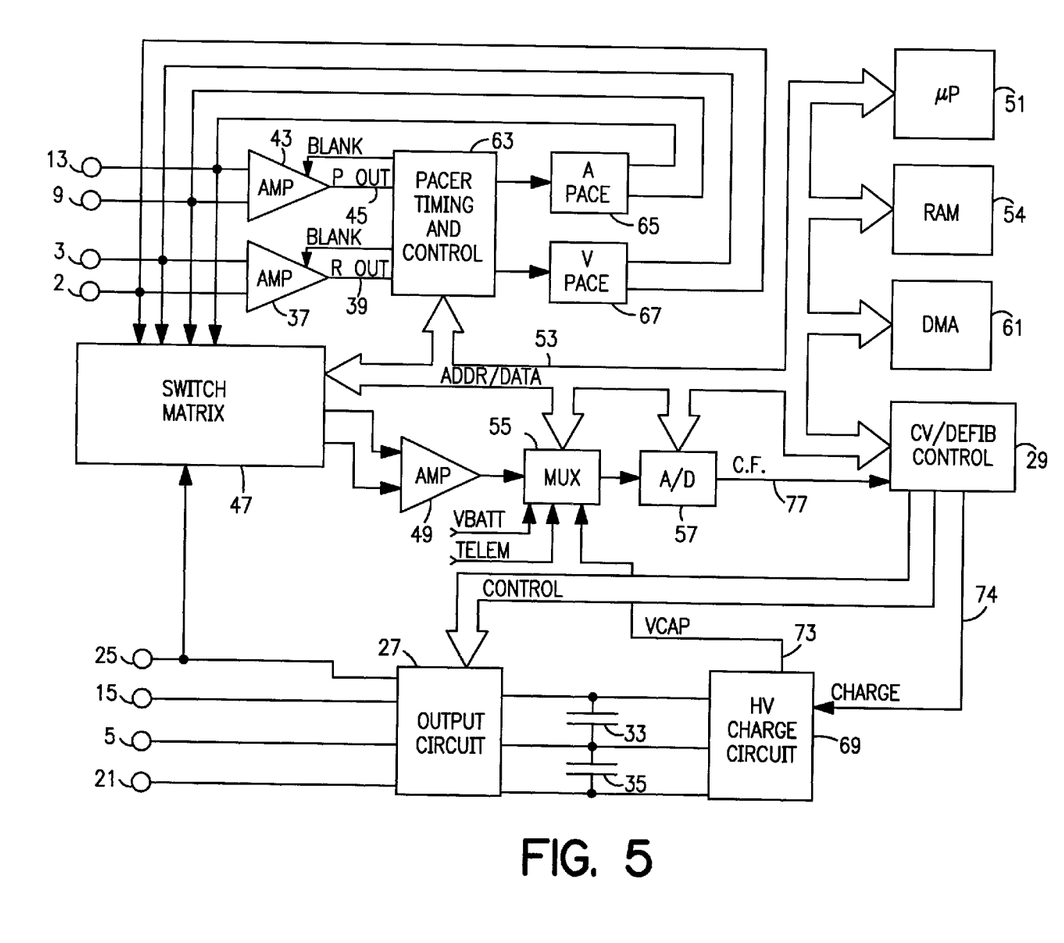
FIG. 5 illustrates a block diagram of the embodiment of FIG. 4, made in accordance with the present invention.

FIGS. 4 and 5 illustrate one embodiment of IMD 10 and a corresponding lead set of the present invention, where IMD 10 is a PCD. In FIG. 4, the ventricular lead takes the form of leads disclosed in the '838 and '430 patents to Bardy, and includes an elongated insulative lead body 1 carrying three concentric coiled conductors separated from one another by tubular insulative sheaths. Located adjacent the distal end of lead 1 are ring electrode 2, extendable helix electrode 3 mounted retractably within insulative electrode head 4 and elongated coil electrode 5. Each of the electrodes is coupled to one of the coiled conductors within lead body 1. Electrodes 2 and 3 are employed for cardiac pacing and for sensing ventricular depolarizations. At the proximal end of the lead is bifurcated connector 6, which carries three electrical connectors, each coupled to one of the coiled conductors. Defibrillation electrode 5 may be fabricated from platinum, platinum alloy or other materials known to be usable in implantable defibrillation electrodes and may be about 5 cm in length.

The atrial/SVC lead shown in FIG. 4 includes elongated insulative lead body 7 carrying three concentric coiled conductors separated from one another by tubular insulative sheaths corresponding to the structure of the ventricular lead. Located adjacent the J-shaped distal end of the lead are ring electrode 9 and extendable helix electrode 13 mounted retractably within an insulative electrode head 15. Each of the electrodes is coupled to one of the coiled conductors within lead body 7. Electrodes 13 and 9 are employed for atrial pacing and for sensing atrial depolarizations. Elongated coil electrode 19 is provided proximal to electrode 9 and coupled to the third conductor within lead body 7. Electrode 19 preferably is 10 cm in length or greater and is configured to extend from the SVC toward the tricuspid valve. In one embodiment of the present invention, approximately 5 cm of the right atrium/SVC electrode is located in the right atrium with the remaining 5 cm located in the SVC. At the proximal end of the lead is bifurcated connector 17, which carries three electrical connectors, each coupled to one of the coiled conductors.

The coronary sinus lead shown in FIG. 4 assumes the form of a coronary sinus lead disclosed in the above cited '838 patent, and includes elongated insulative lead body 41 carrying one coiled conductor coupled to an elongated coiled defibrillation electrode 21. Electrode 21, illustrated in broken outline in FIG. 4, is located within the coronary sinus and the great vein of the heart. At the proximal end of the lead is connector plug 23 carrying an electrical connector coupled to the coiled conductor. The coronary sinus/great vein electrode 41 may be about 5 cm in length.

Implantable PCD 10 is shown in FIG. 4 in combination with leads 1, 7 and 41, and lead connector assemblies 23, 17 and 6 inserted into connector block 12. Optionally, insulation of the outward facing portion of housing 14 of PCD 10 may be provided using a plastic coating such as parylene or silicone rubber, as is employed in some unipolar cardiac pacemakers. The outward facing portion, however, may be left uninsulated or some other division between insulated and uninsulated portions may be employed. The uninsulated portion of housing 14 serves as a subcutaneous defibrillation electrode to defibrillate either the atria or ventricles. Lead configurations other that those shown in FIG. 4 may be practiced in conjunction with the present invention, such as those shown in U.S. Pat. No. 5,690,686 to Min et al., hereby incorporated by reference in its entirety.

FIG. 5 is a functional schematic diagram of one embodiment of implantable PCD 10 of the present invention. This diagram should be taken as exemplary of the type of device in which various embodiments of the present invention may be embodied, and not as limiting, as it is believed that the invention may be practiced in a wide variety of device implementations, including cardioverter and defibrillators which do not provide anti-tachycardia pacing therapies.

PCD 10 is provided with an electrode system. If the electrode configuration of FIG. 4 is employed, the correspondence to the illustrated electrodes is as follows. Electrode 25 in FIG. 5 includes the uninsulated portion of the housing of PCD 10. Electrodes 25, 15, 21 and 5 are coupled to high voltage output circuit 27, which includes high voltage switches controlled by CV/defib control logic 29 via control bus 31. Switches disposed within circuit 27 determine which electrodes are employed and which electrodes are coupled to the positive and negative terminals of the capacitor bank (which includes capacitors 33 and 35) during delivery of defibrillation pulses.

Electrodes 2 and 3 are located on or in the ventricle and are coupled to the R-wave amplifier 37, which preferably takes the form of an automatic gain controlled amplifier providing an adjustable sensing threshold as a function of the measured R-wave amplitude. A signal is generated on R-out line 39 whenever the signal sensed between electrodes 2 and 3 exceeds the present sensing threshold.

Electrodes 9 and 13 are located on or in the atrium and are coupled to the P-wave amplifier 43, which preferably also takes the form of an automatic gain controlled amplifier providing an adjustable sensing threshold as a function of the measured P-wave amplitude. A signal is generated on P-out line 45 whenever the signal sensed between electrodes 9 and 13 exceeds the present sensing threshold. The general operation of R-wave and P-wave amplifiers 37 and 43 may correspond to that disclosed in U.S. Pat. No. 5,117,824, by Keimel et al., issued Jun. 2, 1992, for "An Apparatus for Monitoring Electrical Physiologic Signals," hereby incorporated by reference in its entirety.

Switch matrix 47 is used to select which of the available electrodes are coupled to wide band (0.5–200 Hz) amplifier 49 for use in digital signal analysis. Selection of electrodes is controlled by the processor 51 via data/address bus 53, which selections may be varied as desired. Signals from the electrodes selected for coupling to bandpass amplifier 49 are provided to multiplexer 55, and thereafter converted to multi-bit digital signals by A/D converter 57, for storage in RAM 59 under control of direct memory access circuit 61. Microprocessor 51 may employ digital signal analysis techniques to characterize the digitized signals stored in RAM 59 to recognize and classify the patient's heart rhythm employing any of the numerous signal processing methodologies known to the art.

The remainder of the circuitry is dedicated to the provision of cardiac pacing, cardioversion and defibrillation therapies, and, for purposes of the present invention, may correspond to circuitry known to those skilled in the art. The following exemplary apparatus is disclosed for accomplishing pacing, cardioversion and defibrillation functions. Pacer timing/control circuitry 63 preferably includes programmable digital counters which control the basic time intervals associated with DDD, VVI, DVI, VDD, AAI, DDI and other modes of single and dual chamber pacing well known to the art. Circuitry 63 also preferably controls escape intervals associated with anti-tachyarrhythmia pacing in both the atrium and the ventricle, employing any anti-tachyarrhythmia pacing therapies known to the art.

Intervals defined by pacing circuitry 63 include atrial and ventricular pacing escape intervals, the refractory periods during which sensed P-waves and R-waves are ineffective to restart timing of the escape intervals and the pulse widths of the pacing pulses. The durations of these intervals are determined by processor 51, in response to stored data in memory 59 and are communicated to pacing circuitry 63 via address/data bus 53. Pacer circuitry 63 also determines the amplitude of the cardiac pacing pulses under control of processor 51.

During pacing, escape interval counters within pacer timing/control circuitry 63 are reset upon sensing of R-waves and P-waves as indicated by a signals on lines 39 and 45, and in accordance with the selected mode of pacing on time-out trigger generation of pacing pulses by pacer output circuitry 65 and 67, which are coupled to electrodes 9, 13, 2 and 3. Escape interval counters are also reset on the generation of pacing pulses and thereby control the basic timing of cardiac pacing functions, including anti-tachyarrhythmia pacing. The durations of the intervals defined by escape interval timers are determined by processor 51 via data/address bus 53. The value of the count present in the escape interval counters when reset by sensed R-waves and P-waves may be used to measure the durations of R-R intervals, P-P intervals, P-R intervals and R-P intervals, which measurements are stored in memory 59 and used to detect the presence of tachyarrhythmias.

Microprocessor 51 most preferably operates as an interrupt driven device, and is responsive to interrupts from pacer timing/control circuitry 63 corresponding to the occurrence sensed P-waves and R-waves and corresponding to the generation of cardiac pacing pulses. Those interrupts are provided via data/address bus 53. Any necessary mathematical calculations to be performed by processor 51 and any updating of the values or intervals controlled by pacer timing/control circuitry 63 take place following such interrupts.

Detection of atrial or ventricular tachyarrhythmias, as employed in the present invention, may correspond to any of the various tachyarrhythmia detection algorithms presently known in the art. For example, the presence of an atrial or ventricular tachyarrhythmia may be confirmed by detecting a sustained series of short R-R or P-P intervals of an average rate indicative of tachyarrhythmia or an unbroken series of short R-R or P-P intervals. The suddenness of onset of the detected high rates, the stability of the high rates, and a number of other factors known in the art may also be measured at this time. Appropriate ventricular tachyarrhythmia detection methodologies measuring such factors are described in U.S. Pat. No. 4,726,380 issued to Vollmann, U.S. Pat. No. 4,880,005, issued to Pless et al. and U.S. Pat. No. 4,830,006, issued to Haluska et al., all hereby incorporated by reference, each in their respective entirety. An additional set of tachycardia recognition methodologies is disclosed in the article "Onset and Stability for Ventricular Tachyarrhythmia Detection in an Implantable Pacer-Cardioverter-Defibrillator" by Olson et al., published in Computers in Cardiology, Oct. 7–10, 1986, *IEEE Computer Society Press*, pp. 167–170, also hereby incorporated by reference in its entirety. Atrial fibrillation detection methodologies are disclosed in Published PCT Application Ser. No. US92/02829, Publication No. WO92/18198, by Adams et al., and in the article "Automatic Tachycardia Recognition", by Arzbaecher et al., published in PACE, May-June, 1984, pp. 541–547, both of which are hereby incorporated by reference in their entireties.

In the event an atrial or ventricular tachyarrhythmia is detected and an anti-tachyarrhythmia pacing regimen is desired, appropriate timing intervals for controlling generation of anti-tachyarrhythmia pacing therapies are loaded from processor 51 into the pacer timing and control circuitry 63, to control the operation of the escape interval counters therein and to define refractory periods during which detection of R-waves and P-waves is ineffective to restart the escape interval counters.

Alternatively, circuitry for controlling the timing and generation of anti-tachycardia pacing pulses as described in U.S. Pat. No. 4,577,633, issued to Berkovits et al. on Mar. 25, 1986, U.S. Pat. No. 4,880,005, issued to Pless et al. on Nov. 14, 1989, U.S. Pat. No. 4,726,380, issued to Vollmann et al. on Feb. 23, 1988 and U.S. Pat. No. 4,587,970, issued to Holley et al. on May 13, 1986, all of which are hereby incorporated by reference in their entireties, may also be employed.

In the event that the generation of a cardioversion or defibrillation pulse is required, processor 51 may employ an escape interval counter to control timing of such cardioversion and defibrillation pulses, as well as the associated refractory periods. In response to the detection of atrial or ventricular fibrillation or tachyarrhythmia requiring a cardioversion pulse, processor 51 activates cardioversion/defibrillation control circuitry 29, which initiates charging of the high voltage capacitors 33 and 35 via charging circuit 69, under the control of high voltage charging control line 71. The voltage on the high voltage capacitors is monitored via VCAP line 73, which is passed through multiplexer 55 and in response to reaching a predetermined value set by processor 51, results in generation of a logic signal on Cap Full (CF) line 77 to terminate charging. Thereafter, timing of the delivery of the defibrillation or cardioversion pulse is controlled by pacer timing/control circuitry 63. Following delivery of the fibrillation or tachycardia therapy, processor 51 returns the device to q cardiac pacing mode and awaits the next successive interrupt due to pacing or the occurrence of a sensed atrial or ventricular depolarization.

Several embodiments of appropriate systems for the delivery and synchronization of ventricular cardioversion and defibrillation pulses and for controlling the timing functions related to them are disclosed in U.S. Pat. No. 5,188,105 to Keimel, U.S. Pat. No. 5,269,298 to Adams et al. and U.S. Pat. No. 4,316,472 to Mirowski et al., all of which are hereby incorporated by reference, each in its respective entirety. Any known cardioversion or defibrillation pulse control circuitry is believed to be usable in conjunction with various embodiments of the present invention, however. For example, circuitry controlling the timing and generation of cardioversion and defibrillation pulses such as that disclosed in U.S. Pat. No. 4,384,585 to Zipes, U.S. Pat. No. 4,949,719 to Pless et al., or U.S. Pat. No. 4,375,817 to Engle et al., all hereby incorporated by reference in their entireties, may also be employed.

Continuing to refer to FIG. 5, delivery of cardioversion or defibrillation pulses may be accomplished by output circuit 27 under the control of control circuitry 29 via control bus 31. Output circuit 27 determines whether a monophasic or biphasic pulse is delivered, the polarity of the electrodes and which electrodes are involved in delivery of the pulse. Output circuit 27 also includes high voltage switches which control whether electrodes are coupled together during delivery of the pulse. Alternatively, electrodes intended to be coupled together during the pulse may simply be permanently coupled to one another, either exterior to or within the interior of the device housing, and polarity may similarly be pre-set, as in current implantable defibrillators. An example of output circuitry for delivery of biphasic pulse regimens to multiple electrode systems may be found in U.S. Pat. No. 4,953,551, issued to Mehra and in U.S. Pat. No. 4,727,877, both of which are hereby incorporated by reference in their entireties.

An example of circuitry which may be used to control delivery of monophasic pulses is disclosed in U.S. Pat. No. 5,163,427 to Keimel, also hereby incorporated by reference in its entirety. Output control circuitry similar to that disclosed in the '551 Patent or in U.S. Pat. No. 4,800,883 to Winstrom, both of which are hereby incorporated by reference in their entireties, may also be used in conjunction with various embodiments of the present invention to deliver biphasic pulses.

Alternatively, IMD 10 may be an implantable nerve stimulator or muscle stimulator, such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference, each in their respective entireties. The present invention is believed to find wide application to any form of implantable electrical device for use in conjunction with electrical leads.

Output circuit 27 also includes high voltage switches which control whether electrodes are coupled together during delivery of the pulse. Alternatively, electrodes intended to be coupled together during the pulse may simply be permanently coupled to one another, either exterior to or interior of the device housing, and polarity may similarly be pre-set, as in current implantable defibrillators. An example of output circuitry for delivery of biphasic pulse regimens to multiple electrode systems may be found in the above cited patent issued to Mehra and in U.S. Pat. No. 4,727,877, hereby incorporated by reference herein in its entirety.

An example of circuitry which may be used to control delivery of monophasic pulses is disclosed in U.S. Pat. No. 5,163,427 to Keimel, also incorporated by reference herein in its entirety. Output control circuitry similar to that disclosed in U.S. Pat. No. 4,953,551 to Mehra et al. or U.S. Pat. No. 4,800,883 to Winstrom, both incorporated by reference herein in their entireties, may also be used in conjunction with various embodiments of the present invention to deliver biphasic pulses.

Alternatively, IMD 10 may be an implantable nerve stimulator or muscle stimulator such as that disclosed in U.S. Pat. No. 5,199,428 to Obel et al., U.S. Pat. No. 5,207,218 to Carpentier et al. or U.S. Pat. No. 5,330,507 to Schwartz, or an implantable monitoring device such as that disclosed in U.S. Pat. No. 5,331,966 issued to Bennet et al., all of which are hereby incorporated by reference herein, each in its respective entirety. The present invention is believed to find wide application to any form of implantable electrical device for use in conjunction with electrical leads.

Another feature of the IMD 10 is to determine a noise floor. A noise floor is a level corresponding to the absolute value of the greater of a maximum or minimum amplitude of background noise. These amplitudes are preferably detected by the sensing leads 7 implanted in the mammalian heart 8, as described above, and transmitted to the processor 64. Once a noise floor has been determined, the value of the noise floor will represent the lower boundary for further event detection by the IMD 10. The time period from which the noise floor is determined is preferably programmed to occur periodically. For example, the noise floor may be determined during a period when the patient is asleep or other period when the bio-electrical noise level is at a low level. The noise floor represents a value which may be adjusted according to changing background noise levels. However, if the background noise level may be consistently maintained at a minimal value, the noise floor may be assigned a fixed value.

Figure 6:
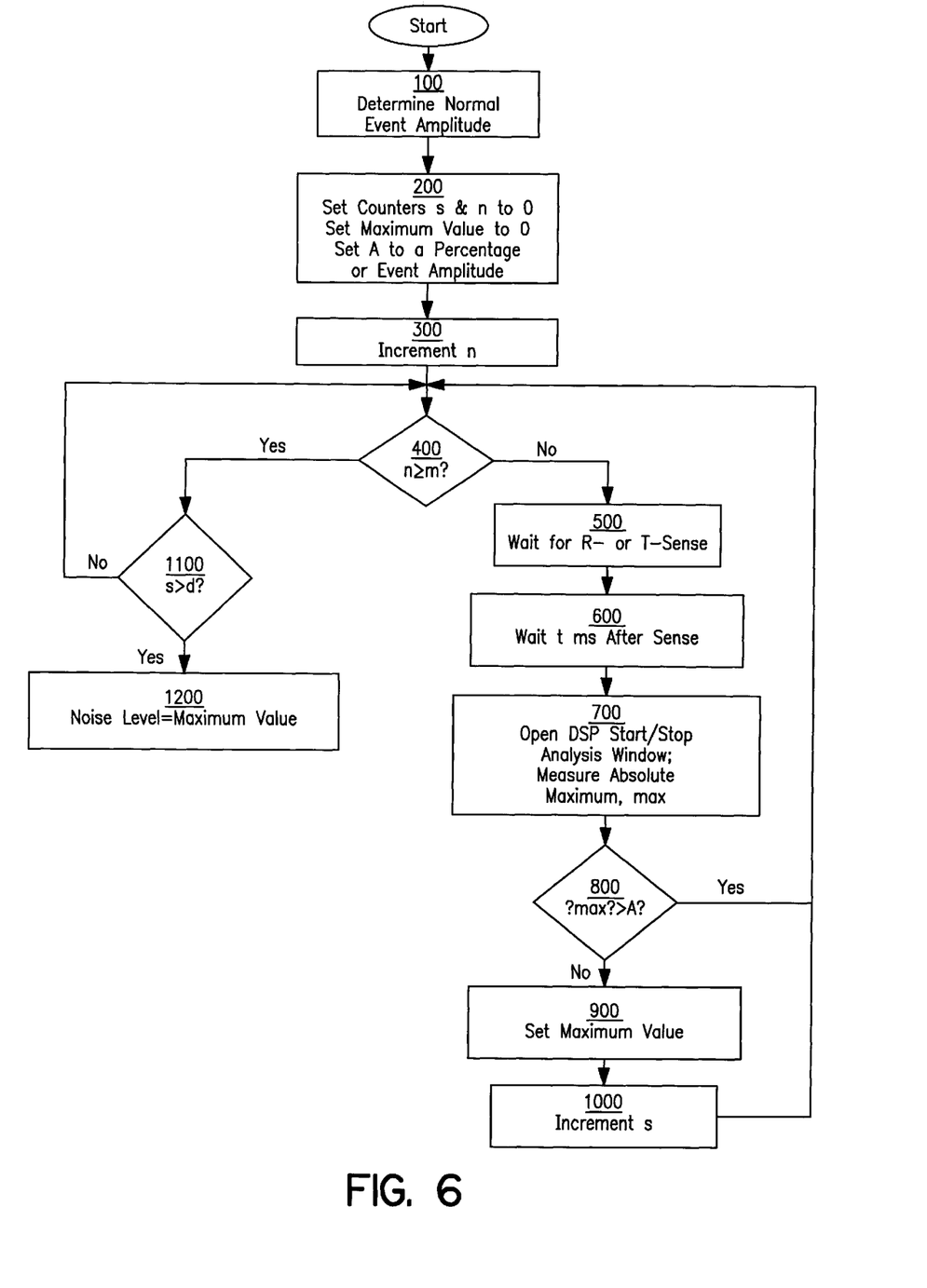
FIG. 6 illustrates a flow chart of a method for determining a representative noise floor, in accordance with the present invention.
Figure 7:
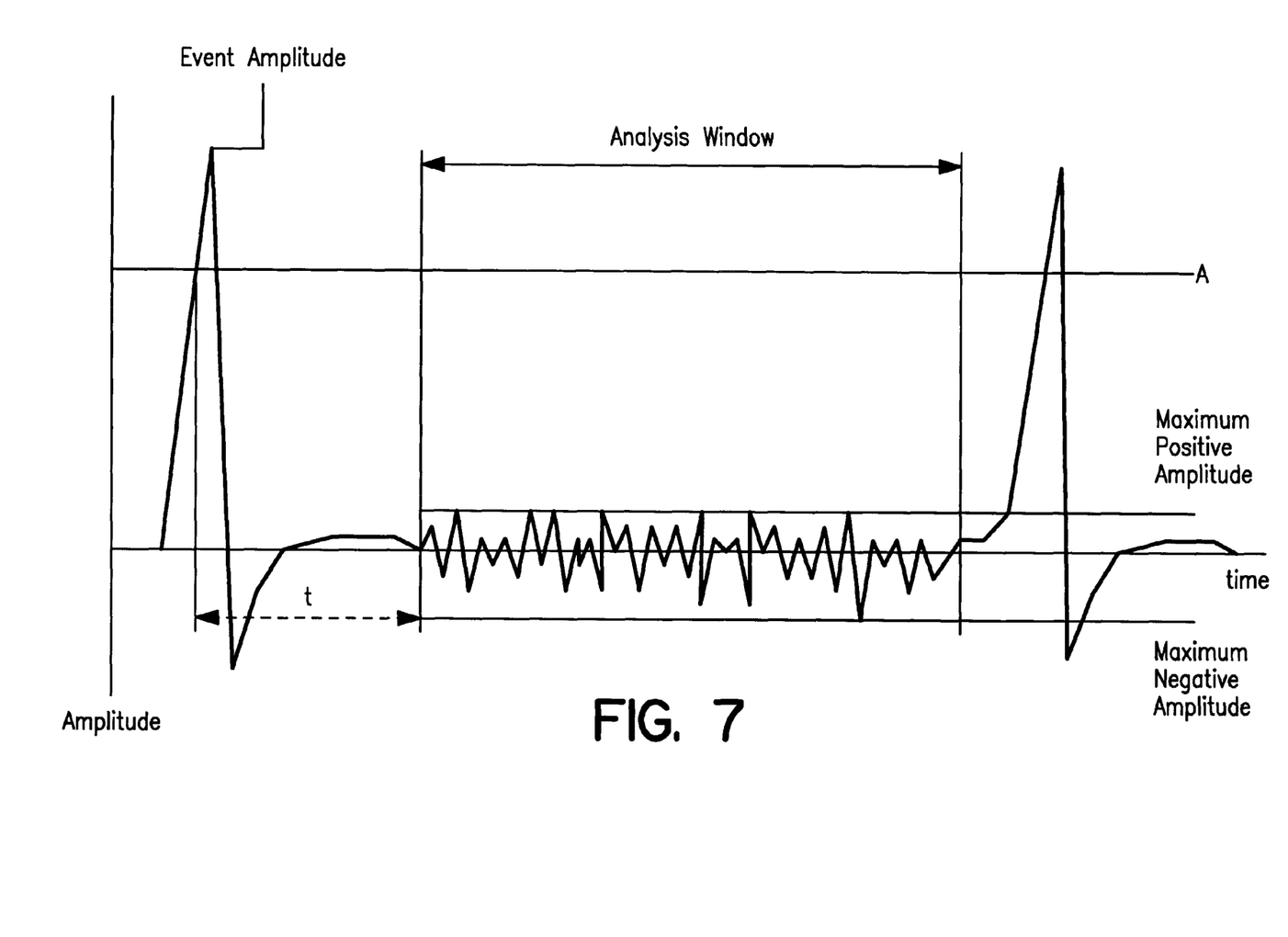
FIG. 7 illustrates a graphical representation of the method of FIG. 6.

FIGS. 6 and 7 illustrate a method for determining a noise floor for atrium or ventricle in a cardiac pacing system from which future atrial or ventricular events may be measured, in accordance with the present invention. In Block 100 of FIG. 6, the processor 64 of the IMD 10 determines a normal event amplitude. Preferably, the normal event amplitude corresponds to the positive and negative amplitude of a monitored event, such as, for example, a beat of the mammalian heart 8. Please refer to FIG. 7 for a graphical representation.

At a predetermined time period after the occurrence of the event (shown as t in FIG. 7), the processor 64 initiates a Digital Signal Processing (DSP) analysis window from which to measure background noise. The analysis window exists for a predetermined time period. During this time period, signals sent from the sensing lead 7 are analyzed. After the predetermined time period expires, the analysis window closes.

It is preferable that, to incorporate the expected noise contribution of the DC/DC converter, the start of the analysis window be as close to the IMD's 10 pace sequence as possible.

Furthermore, the time periods corresponding to the length of the analysis window, including beginning the analysis window and ending the analysis window are preset by the IMD 10. Additionally, these time periods may be adjustable. For example, it is proposed to start the collection of noise data 200 ms after completion of the cardiac cycle to avoid FFRWs being measured as noise in the atrium.

On the contrary, if FFRWs cannot be differentiated from P-waves by other means, it might prove beneficial to incorporate FFRWs in the analysis window.

In Block 200, the processor 64 determines a percentage of the event amplitude. Preferably, this percentage corresponds to a fraction of the event amplitude, and may preferably represent, for example, 10–50% of the event amplitude. Any predetermined percentage may be determined. See, for example, reference A in FIG. 7. The purpose of determining the percentage is such that the processor 64 may ignore any sensed noises above the percentage as it attempts to determine the noise floor. Additionally, the event amplitude percentage provides a starting point for the determination of the noise floor. That is, as a result of the event amplitude percentage, the processor 64 may determine the noise floor to be below the event amplitude percentage, thereby lowering the level from which the processor 64 measures future events. Also in Block 200, the processor 64 initiates a first counter, n, and a second counter, s. The purpose of the two counters is to ensure that the processor 64 records an appropriate number of noise level measurements (the n counter), as well as an appropriate number of allowable (or satisfactory) noise level measurements (the s counter).

After incrementing the first counter, indicating the initiation of a noise level measurement (Block 300), the processor 64, in Block 400, determines whether the first counter, n, is greater or less than the number of measurements required, m. Preferably, the number of measurements required to be taken is predetermined by the IMD 10, and may be adjustable. For example, the IMD 10 may be required to review a total of 50 measurements prior to determining the noise floor.

If the first counter is less than the required number of measurements, in Block 500, the processor 64 waits until it receives a signal from the sensing lead 7. Preferably, the signal sensed by the sensing lead corresponds to an R- or a T-sense. As detailed above, an R- or T-sense corresponds to an event, which may be, for example, a heartbeat. After receiving the signal from the sensing lead 7, in Block 600, the processor 64 waits a predetermined number of milliseconds. See, for example, reference t in FIG. 7. The predetermined number of milliseconds, t, may be determined according to methods described above, and corresponds to the time between the event occurrence and the preferred opening of the analysis window.

After such time has expired, the processor 64 then opens a DSP start/stop analysis window (Block 700). This window is shown graphically in FIG. 7. Additionally in Block 700, the processor 64 then measures the maximum and minimum amplitude values of the background noise, as received from the sensing lead 7. The maximum and minimum amplitude values of the background noise preferably correspond to the maximum positive amplitude and maximum negative amplitude, respectively. As will be shown below, calculations involving these numbers are expressed as absolute values, thus removing the positive/negative indicators of the amplitudes. In the example shown in FIG. 7, the absolute amplitude corresponds to the maximum negative amplitude. Alternatively, the absolute amplitude may correspond to a maximum positive amplitude.

In Block 800, the processor 64 determines whether the absolute amplitude of a measured noise level is greater than the event amplitude percentage. This is to ensure that the measured noise level is below the event amplitude percentage, A, and also to determine whether the measured noise level will be registered. If the absolute amplitude of the measured noise level is indeed greater than the event amplitude percentage, then the processor 64 ignores the measured noise level, and returns to Block 300 to analyze the next noise level received from the sensing lead 7.

If the absolute amplitude of the measured noise level is less than or equal to the event amplitude percentage (meaning that the measured absolute amplitude will be considered in the determination of the noise level), in Block 900, the processor 64 then compares the absolute amplitude with a previously saved maximum value, and resets the maximum value to the larger of the two compared values. The purpose of this step is to keep a continuously running record of the maximum value. Thus, only if the absolute amplitude is larger than the previously saved maximum value will the absolute amplitude be substituted for the previously saved maximum value. Upon resetting (or maintaining) the maximum value, the processor 64, in Block 1000, increments the second counter, s, indicating that a satisfactory measurement has been taken.

If Block 400 indicates that the number of noise level measurements is greater than or equal to the required number of noise level measurements, the processor 64 then determines whether the first counter (indicating the number of satisfactory measurements) is greater than a predetermined number of required valid measurements, d (Block 1100). The predetermined number of required valid measurements is preferably preset by the IMD 10, and may be adjusted. If the first counter is less than or equal to than a predetermined number of valid measurements, the IMD 10 returns to Block 300, and continues to take measurements until it reaches the required number of valid measurements.

If the first counter is greater than a predetermined number of valid measurements, the processor 64 resets the noise floor to the maximum value, as obtained in Block 900 above (Block 1200). It should be noted that the noise floor may additionally include a safety factor, corresponding to a predetermined level above the noise floor set in Block 1200. The safety factor acts as a buffer between the noise floor and a future recorded event, ensuring that future background noise may not wrongly be classified as an event.

The preceding specific embodiments are illustrative of the practice of the invention. It is to be understood, therefore, that other expedients known to those skilled in the art or disclosed herein, may be employed without departing from the invention or the scope of the appended claims. For example, the present invention is not limited to determining a representative noise floor in a cardiac pacing system. The present invention is also not limited to determination algorithms per se, but may find further application as a means for measuring other indications of a cardiac system. The present invention further includes within its scope methods of making and using the method and system for determining a representative noise floor in a cardiac pacing system described above.

In the claims, means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts a nail and a screw are equivalent structures.

All printed publications, patent applications and patents referenced hereinabove are incorporated by reference herein, each in its respective entirety.

We claim:

1. A method for determining a representative noise floor in a cardiac pacing system in which future events are measured, comprising:
    sensing a cardiac signal;
    determining an event amplitude of the cardiac signal;
    recording a plurality of noise levels when each of the plurality of noise levels is less than a predetermined percentage of the event amplitude; and
    determining, using a DSP, the noise floor as an absolute maximum value of the recorded noise level having the largest amplitude.

2. The method of claim 1, further comprising determining the noise floor as a function of the absolute maximum value of the recorded noise level having the largest amplitude and a safety factor.

3. The method of claim 2, wherein the safety factor is a predetermined value above the noise floor.

4. The method of claim 1, further comprising commencing the recording of the plurality of noise levels at a first predetermined time after the cardiac signal has occurred.

5. The method of claim 5, further comprising terminating the recording of the plurality of noise levels at a second predetermined time after the cardiac signal has occurred.

6. The method of claim 1, further comprising determining the noise floor periodically.

7. The method of claim 1, wherein the percentage is between 10 and 50 percent.

8. The method of claim 1, wherein the absolute maximum value comprises the largest absolute value of each of the plurality of noise levels.

9. An implantable medical device, comprising:
    a processor for receiving and recording a plurality of recorded noise levels;
    a DSP operably connected to the processor; and
    at least one sensing lead for sensing the noise levels and sensing cardiac signals having an event amplitude, the sensing lead being operably connected to the processor;
    wherein a noise floor is determined by the DSP as an absolute maximum value of the largest amplitude signal among the plurality of recorded noise levels received by the processor from the at least one sensing lead, each of the plurality of recorded noise levels being below a percentage of the event amplitude sensed by the sensing lead and received by the processor.

10. The implantable medical device of claim 9, wherein the noise floor further comprises the sum of the absolute maximum value of the largest amplitude signal and a safety factor.

11. The implantable medical device of claim 10, wherein the safety factor is predetermined value corresponding to a level above the noise floor.

12. The implantable medical device of claim 9, wherein the processor further begins recording the plurality of noise levels at a first predetermined time after the cardiac signal has been sensed by the sensing lead and received by the processor.

13. The implantable medical device of claim 12, wherein the processor further ends recording the plurality of noise levels at a second predetermined time after the cardiac signal has occurred.

14. The implantable medical device of claim 9, wherein the DSP further determines the noise floor periodically.

15. The implantable medical device of claim 9, wherein the percentage is between 10 and 50 percent.

16. The implantable medical device of claim 9, wherein the absolute maximum value comprises the largest absolute value of each of the plurality of noise levels.

17. An implantable medical device system, comprising:
   means for determining an event amplitude of a cardiac signal;
   means for recording a plurality of noise levels when each of the plurality of noise levels is less than a predetermined percentage of the event amplitude; and
   DSP means for determining the noise floor as an absolute maximum value of the largest amplitude signal among the plurality of recorded noise levels.

18. The implantable medical device system of claim 17, further comprising means for determining the noise floor as a function of the absolute maximum value of the largest amplitude signal among the plurality of recorded noise levels and a safety factor.

19. The implantable medical device system of claim 18, wherein the safety factor is a predetermined value above the noise floor.

20. The implantable medical device system of claim 17, further comprising means for commencing the recording of the plurality of noise levels at a first predetermined time after the cardiac signal has occurred.

21. The implantable medical device system of claim 20, further comprising means for terminating the recording of the plurality of noise levels at a second predetermined time after the cardiac signal has occurred.

22. The implantable medical device system of claim 17, further comprising means for determining the noise floor periodically.

23. The implantable medical device system of claim 17, wherein the percentage is between 10 and 50 percent.

24. The implantable medical device system of claim 17, wherein the maximum absolute value comprises the absolute value of the largest amplitude signal among the plurality of recorded noise levels.

* * * * *